(12) United States Patent
Nielsen et al.

(10) Patent No.: US 10,888,009 B2
(45) Date of Patent: Jan. 5, 2021

(54) METHOD OF FORMING A SEALED PACKAGE

(71) Applicant: Medtronic, Inc., Minneapolis, MN (US)

(72) Inventors: Christian S. Nielsen, River Falls, WI (US); Rajesh V. Iyer, Eden Prairie, MN (US); Gordon O. Munns, Stacy, MN (US); Andrew J. Ries, Lino Lakes, MN (US); Andrew J. Thom, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/171,776

(22) Filed: Oct. 26, 2018

(65) Prior Publication Data

US 2020/0137910 A1     Apr. 30, 2020

(51) Int. Cl.
| | |
|---|---|
| *H05K 5/06* | (2006.01) |
| *A61N 1/375* | (2006.01) |
| *A61N 1/378* | (2006.01) |
| *H01M 2/30* | (2006.01) |
| *H05K 5/00* | (2006.01) |
| *H05K 7/14* | (2006.01) |

(52) U.S. Cl.
CPC ............ *H05K 5/069* (2013.01); *A61N 1/378* (2013.01); *A61N 1/3758* (2013.01); *H01M 2/30* (2013.01); *H05K 5/0086* (2013.01); *H05K 7/1417* (2013.01); *H01M 2220/30* (2013.01)

(58) Field of Classification Search
CPC ............... H05K 5/0086; A61N 1/3758; H01M 2220/30
See application file for complete search history.

(56) References Cited

U.S. PATENT DOCUMENTS

| | | |
|---|---|---|
| 5,407,119 A | 4/1995 | Churchill et al. |
| 5,503,703 A | 4/1996 | Dahotre et al. |
| 5,513,793 A | 5/1996 | Malmgren |
| 5,738,270 A | 4/1998 | Malmgren |
| 6,586,704 B1 | 7/2003 | Cockeram et al. |
| 9,421,303 B2 | 8/2016 | Bailey et al. |

(Continued)

OTHER PUBLICATIONS

(PCT/US2019/057374) PCT Notification of Transmittal of the International Search Report and the Written Opinion of the International Searching Authority, dated Feb. 5, 2020, 10 pages.

*Primary Examiner* — Jay C Chang
*Assistant Examiner* — Mikka Liu
(74) *Attorney, Agent, or Firm* — Mueting Raasch Group (57) ABSTRACT

Various embodiments of a sealed package and a method of forming such package are disclosed. The package includes a housing having an inner surface and an outer surface, a dielectric substrate having a first major surface and a second major surface, and a dielectric bonding ring disposed between the first major surface of the dielectric substrate and the housing, where the dielectric bonding ring is hermetically sealed to both the first major surface of the dielectric substrate and the housing. The package further includes an electronic device disposed on the first major surface of the dielectric substrate, and a power source disposed at least partially within the housing and electrically connected to the electronic device.

14 Claims, 6 Drawing Sheets

(56) References Cited

U.S. PATENT DOCUMENTS

| | | | |
|---|---|---|---|
| 2005/0116586 A1* | 6/2005 | Tanaya | H03H 9/21 |
| | | | 310/348 |
| 2012/0068578 A1* | 3/2012 | Takahashi | H03H 3/02 |
| | | | 310/344 |
| 2012/0112329 A1* | 5/2012 | Yen | H01L 31/0203 |
| | | | 257/666 |
| 2015/0027168 A1* | 1/2015 | Dabich, II | B23K 26/206 |
| | | | 65/41 |
| 2016/0126201 A1* | 5/2016 | Arvin | H01L 24/11 |
| | | | 257/773 |
| 2016/0185081 A1 | 6/2016 | Sandlin et al. | |
| 2016/0260938 A1 | 9/2016 | Nielsen et al. | |
| 2017/0127543 A1* | 5/2017 | Day | H01M 2/30 |
| 2018/0279924 A1 | 10/2018 | Kuhn | |

* cited by examiner

METHOD OF FORMING A SEALED PACKAGE

TECHNICAL FIELD

This disclosure generally relates to sealed packages and methods of forming such packages.

BACKGROUND

Various systems require electrical coupling between electrical devices disposed within a sealed enclosure or housing and devices or systems external to the enclosure. Oftentimes, such electrical coupling needs to withstand various environmental factors such that a conductive pathway or pathways from the external surface of the enclosure to within the enclosure remains stable. For example, implantable medical devices (IMDs), e.g., cardiac pacemakers, defibrillators, neurostimulators, and drug pumps, which include electronic circuitry and one or more power sources, require an enclosure or housing to contain and seal these elements within a body of a patient. Many of these IMDs include one or more electrical feedthrough assemblies to provide electrical connections between the elements contained within the housing and components of the IMD external to the housing, for example, one or more sensors, electrodes, and lead wires mounted on an exterior surface of the housing, or electrical contacts housed within a connector header, which is mounted on the housing to provide coupling for one or more implantable leads. Such leads typically carry one or more electrodes and/or one or more other types of physiological sensors. A physiological sensor, for example a pressure sensor, incorporated within a body of a lead may also require a hermetically-sealed housing to contain electronic circuitry of the sensor and an electrical feedthrough assembly to provide electrical connection between one or more lead wires, which extend within the implantable lead body, and the contained circuitry.

SUMMARY

The techniques of this disclosure generally relate to a hermetically-sealed package and a method of forming such package. The hermetically-sealed package can include a bonding ring disposed between a first major surface of a substrate and a housing of the package. The bonding ring, which in one or more embodiments can be a dielectric bonding ring, is hermetically sealed to both the first major surface of the substrate and the housing. The package can also include one or more electronic devices disposed on one or both of the first major surface and a second major surface of the substrate, and a power source disposed at least partially within the housing, where the power can be electrically connected to the electronic device.

In one example, aspects of this disclosure relate to a method of forming a hermetically-sealed package. The method includes disposing a cavity in a housing wafer, hermetically sealing a dielectric bonding wafer to a first major surface of the housing wafer and disposing an opening in the dielectric bonding wafer to expose the cavity of the housing wafer. The method further includes disposing an electronic device on a substrate wafer, and hermetically sealing the substrate wafer to the dielectric bonding wafer such that the electronic device is in registration with the cavity of the housing wafer.

In another example, aspects of this disclosure relate to a hermetically-sealed package. The package includes a housing having an inner surface and an outer surface, a dielectric substrate having a first major surface and a second major surface, and a dielectric bonding ring disposed between the first major surface of the dielectric substrate and the housing, where the dielectric bonding ring is hermetically sealed to both the first major surface of the dielectric substrate and the housing. The package further includes an electronic device disposed on the first major surface of the dielectric substrate, and a power source disposed at least partially within the housing and electrically connected to the electronic device.

In another example, aspects of this disclosure relate to a hermetically-sealed package. The package includes a housing having a first major surface, a second major surface, and a cavity disposed in the first major surface, a dielectric substrate having a major surface, and a dielectric bonding ring disposed between the major surface of the dielectric substrate and the second major surface of the housing. The dielectric bonding ring is hermetically sealed to both the major surface of the dielectric substrate and the second major surface of the housing. Further, the dielectric substrate, the dielectric bonding ring, and the second major surface of the housing form a second cavity. The package further includes an electronic device disposed on the major surface of the dielectric substrate and within the second cavity, and a power source disposed at least partially within the cavity of the housing and electrically connected to the electronic device.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.)

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 7A-D are various perspective views of one embodiment of a method of forming the hermetically-sealed package of FIGS. 1-4, were

DETAILED DESCRIPTION

In general, the present disclosure provides various embodiments of a hermetically-sealed package and a method of forming such package. The hermetically-sealed package can include a bonding ring disposed between a first major surface of a substrate and a housing of the package. The bonding ring, which in one or more embodiments can be a dielectric bonding ring, is hermetically sealed to both the first major surface of the substrate and the housing. The package can also include one or more electronic devices disposed on one or both of the first major surface and a second major surface of the substrate, and a power source disposed at least partially within the housing, where the power can be electrically connected to the electronic device.

Some embodiments of sealed packages can include a metallic housing that is bonded to a dielectric substrate to form the sealed package. Such bonding of metallic materials to dielectric materials may require diffusion bonding processes to form a hermetic seal. These diffusion bonding processes can, however, damage electronic components or power sources that may be disposed on the dielectric substrate or within the metallic housing prior to the bonding of the dielectric substrate to the housing. Further, bonding the dielectric substrate to the metallic housing can require a highly polished interface between the substrate and housing such that a bond between the substrate and the housing forms a hermetic seal.

One or more embodiments of hermetically-sealed packages and methods of forming such packages described herein can provide various advantages over currently-available packages and methods. For example, in one or more embodiments, a diffusion bonding process can be utilized to connect a bonding ring to a housing of the package prior to hermetically sealing a dielectric substrate to the bonding ring. The diffusion bonding process can be utilized before an electronic component or power source is disposed on or within the substrate or the housing, thereby protecting the component and power source from such bonding processes. In one or more embodiments, a typical bonding process can be utilized to attach the dielectric substrate to the bonding ring. Such bonding process will be less likely to damage electronic components and power sources that may be disposed on or within the substrate or the housing. Further, the bonding ring can provide a bonding surface that is flat such that the substrate can be hermetically-sealed to the bonding ring to provide a hermetically-sealed package. In one or more embodiments, a bonding process can utilize a highly-localized fusion of materials using, e.g., as pulsed laser.

The various embodiments of sealed packages described herein can include or be utilized with any device or system that requires sealed conductive pathways. For example, one or more embodiments of sealed packages described herein can include an implantable medical device or system disposed within the sealed package. In one or more embodiments, the sealed package can be electrically connected to an implantable medical device. Nearly any implantable medical device or system employing leads may be used with the various embodiments of sealed packages described herein. Representative examples of implantable medical devices included in or utilized with the various embodiments of sealed packages described herein include hearing implants, e.g., cochlear implants; sensing or monitoring devices; signal generators such as cardiac pacemakers or defibrillators; neurostimulators (such as spinal cord stimulators, brain or deep brain stimulators, peripheral nerve stimulators, vagal nerve stimulators, occipital nerve stimulators, subcutaneous stimulators, etc.); gastric stimulators; or the like.

Figure 1:
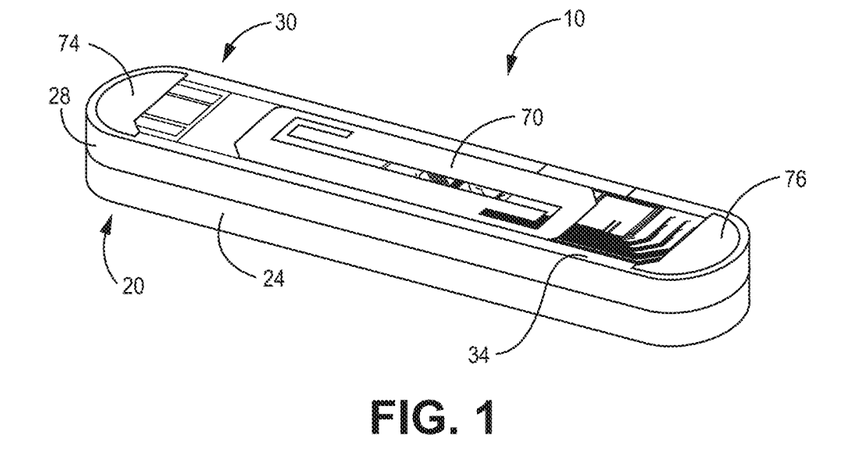
FIG. 1 is a schematic perspective view of one embodiment of a sealed package.
Figure 2:
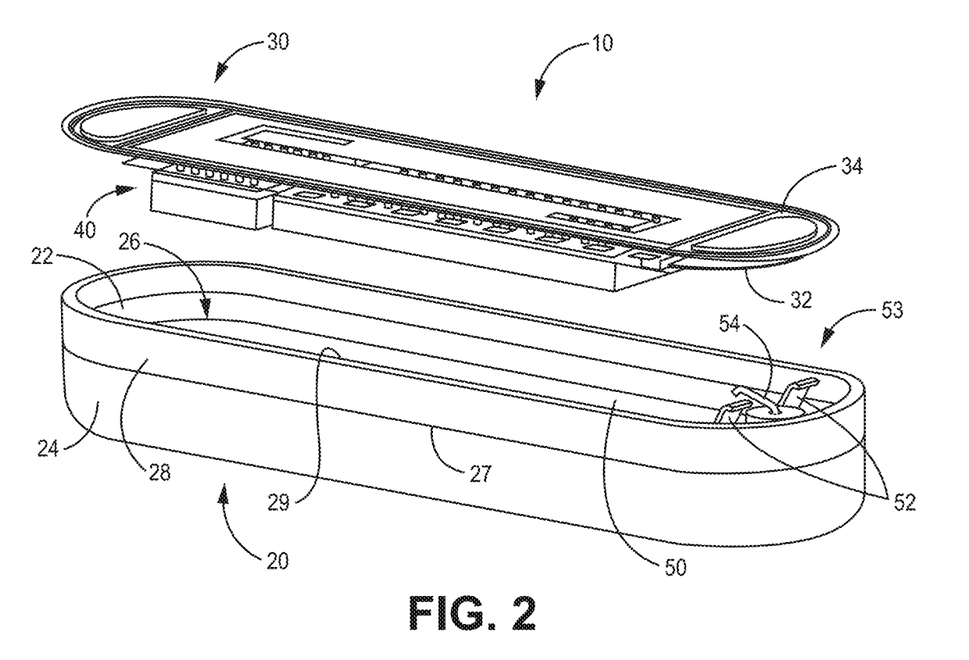
FIG. 2 is a schematic exploded view of the sealed package of FIG. 1.
Figure 3:
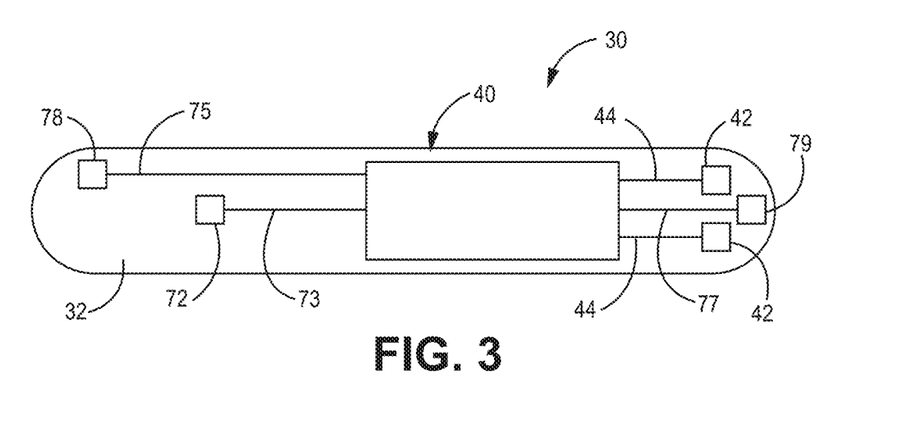
FIG. 3 is a schematic plan view of a first major surface of a substrate of the sealed package of FIG. 1.
Figure 4:
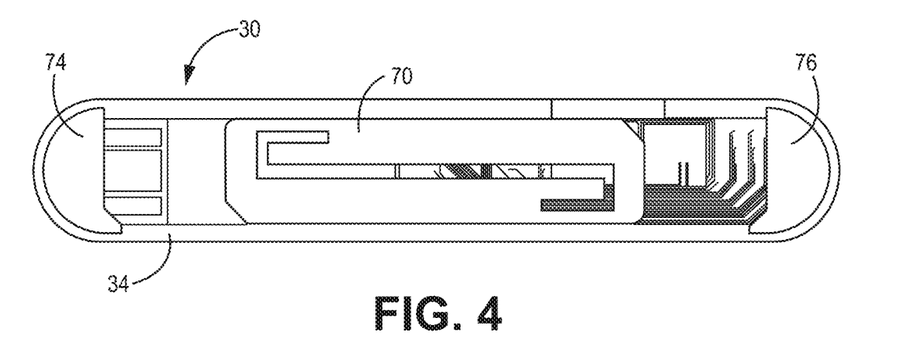
FIG. 4 is a schematic plan view of a second major surface of the substrate of the sealed package of FIG. 1.

FIGS. 1-4 are various schematic views of one embodiment of a sealed package 10. The package 10 includes a housing 20 and a substrate 30. The housing 20 includes an inner surface 22 and an outer surface 24. Further, the substrate 30 includes a first major surface 32 and a second major surface 34. The package 10 also includes at least one electronic device 40 disposed on the first major surface 32 of the substrate 30. The electronic device 40 can include one or more device contacts 42 (FIG. 3). The package 10 also includes a power source 50 that is disposed at least partially within the housing 20. In one or more embodiments, the power source 50 can be disposed within a cavity 26 of the housing 20. The power source 50 includes one or more power source contacts 52, 54 as is further described herein.

The substrate 30 can be sealed to the housing 20. In one or more embodiments, the substrate 30 can be hermetically sealed to the housing 20. Further, in one or more embodiments, the substrate 30 can be sealed to the housing 20 such that a non-bonded electrical connection can be formed between one or more device contacts 42 and one or more power source contacts 52, 54.

The housing 20 can include any suitable material or materials, e.g., metallic, polymeric, ceramic, or inorganic materials. In one or more embodiments, the housing 20 can include at least one of glass, quartz, silica, sapphire, silicon carbide, diamond, MP35N (available from Elgiloy Specialty Metals, Sycamore, Ill.), or gallium nitride. In one or more embodiments, the housing 20 can include at least one of copper, silver, titanium, niobium, zirconium, tantalum, stainless steel, platinum, or iridium. In one or more embodiments, the housing 20 can include the same material or materials as the substrate 30. Further, in one or more embodiments, the housing 20 can include biocompatible materials such that the package 10 can be implanted within a patient's body. Further, one or more coatings or layers can be disposed on the outer surface 24 of the housing that provide biocompatibility. In one or more embodiments, the housing 20 can be electrically conductive to provide a ground electrode for the package 10 as is known in the art. In one or more embodiments, the housing 20 can be non-conductive.

Further, the housing 20 can take any suitable shape or shapes and have any suitable dimensions. In one or more embodiments, the housing 20 takes a shape that forms the cavity 26 that can accommodate the power source 50 (including active material and power source electronics) and electronic device 40 as is further described herein. In one or more embodiments, the cavity 26 can be formed by the inner surface 22 of the housing 20. In embodiments that include the bonding ring 28, the cavity 26 can be in part defined by an inner surface of the bonding ring such that the cavity extends between the housing and the first major surface 32 of the substrate 30.

The housing 20 can be a single, unitary housing. In one or more embodiments, the housing 20 can include two or more parts that are made separately and then connected together using any suitable technique or techniques, e.g., housing 120 of FIG. 5.

Sealed to the housing 20 is the substrate 30. In one or more embodiments, the substrate 30 can be a dielectric substrate such that the electronic device 40, external electrodes 74, 76, and any conductors or other devices disposed on the substrate can be electrically isolated if desired. The substrate 30 can include any suitable material or materials. In one or more embodiments, the substrate can include a dielectric material, e.g., at least one of glass, quartz, silica, sapphire, silicon carbide, diamond, or gallium nitride, or any combinations thereof. In one or more embodiments, the substrate 30 can include the same material or materials as the housing 20. As with the housing 20, the substrate 30 can include a biocompatible material. Further, the substrate 30 can include one or more coatings or layers that can provide biocompatibility.

In one or more embodiments, the substrate 30 can be a transparent substrate. As used herein, the phrase "transparent substrate" refers to a substrate that can transmit a given percentage of electromagnetic radiation incident thereon during use of laser bonding techniques described herein to preferentially heat only an outer surface of the substrate (e.g., first major surface 32 or second major surface 34 of substrate 30), and not an inner bulk of the substrate, and thereby create a bond that has a relatively greater strength than the bulk strength of the substrate. In one or more embodiments, the substrate 30 can be substantially transparent at a desired wavelength or range of wavelengths. As used herein, the phrase "substantially transparent" means that the substrate transmits greater than 50% of electromagnetic radiation incident on the substrate for a selected wavelength or range of wavelengths, assuming no reflection at the air-substrate boundaries. In one or more embodiments, the substrate 30 can be substantially transmissive to electromagnetic radiation having a wavelength of at least 200 nm. In one or more embodiments, the substrate 30 can be substantially transmissive to electromagnetic radiation having a wavelength of greater than 10,000 nm. In one or more embodiments, the substrate 30 can be substantially transmissive to electromagnetic radiation having a wavelength in a range of 200 nm to 10,000 nm. In one or more embodiments, the substrate 30 can be substantially transmissive to at least one of UV light, visible light, or IR light.

The substrate 30 can include any suitable dimensions, e.g., thicknesses. Further, the substrate 30 can take any suitable shape or shapes. In one or more embodiments, the substrate 30 can take a shape or shapes that is complementary to a shape of the housing 20 such that the substrate can be sealed to the housing and provide a low-profile shape for the sealed package 10. Further, the substrate 30 can be a single, unitary substrate or multiple substrates joined together.

Disposed on the first major surface 32 of the substrate 30 is the electronic device 40. Although depicted as being disposed on the first major surface 32, the electronic device 40 can be disposed on the second major surface 34, or one or more electronic devices can be disposed on both the first and second major surfaces. In one or more embodiments, one or more electronic devices can be disposed within the housing 20 and not attached to the substrate 30.

Any suitable electronic device 40 or devices can be disposed on the first major surface 32, e.g., capacitors, transistors, integrated circuits, including controllers and multiplexers, sensors, etc. Further, any suitable number of electronic devices 40 can be disposed on the first major surface 32. Further, any suitable technique or techniques can be utilized to dispose the electronic device 40 on the first major surface 32. In one or more embodiments, the electronic device 40 can be formed on the first major surface 32 of the substrate 30. In one or more embodiments, the device 40 can be formed separately and then attached to the first major surface 32. Any suitable technique or techniques can be utilized to attach the electronic device 40 to the substrate 30, e.g., a bond can be formed between the electronic device and the first major surface 32 of the substrate.

As mentioned herein, the electronic device 40 can include one or more sensors, e.g., one or more optical sensors. In one or more embodiments, at least a portion of the substrate 30 can be transparent such that an optical sensor disposed on the first major surface 32 can detect one or more external signals, e.g., from a patient, when the package 10 is disposed within the patient. In one or more embodiments, the at least a portion of the substrate 30 can be sufficiently transparent to enable transmission of all, or a sufficient magnitude, of the electromagnetic radiation that is incident on the substrate for reception by the optical sensor such that the received light can be processed to detect the external signal. For example, the electronic device 40 can include an infrared or near-infrared oxygen sensor that can detect through the substrate 30 the oxygen level of the blood of the patient.

The electronic device 40 can be electrically connected to one or more additional electronic devices disposed on one or both of the first major surface 32 and second major surface 34 or within the housing 20. For example, the electronic device 40 can be electrically connected to the power source 50 using any suitable technique or techniques. In one or more embodiments, the electronic device 40 can include one or more device contacts 42 that are electrically connected to the electronic device using any suitable technique or techniques. For example, FIG. 3 is a schematic plan view of the first major surface 32 of the substrate 30. Device contacts 42 are electrically connected to device 40 through conductors 44. Although illustrated as including two device contacts 42, the package 10 can include any suitable number of device contacts. The device contacts 42 can include any suitable contacts, pads, terminals, etc., that provide electrical connection to other devices, e.g., power source 50. The contacts 42 can take any suitable shape or shapes and be disposed in any suitable location on or in the first major surface 32 of the substrate 30. Any suitable technique or techniques can be utilized to form device contacts 42 and conductors 44, e.g., chemical vapor deposition, plasma vapor deposition, physical vapor deposition, etc., followed by photolithography, chemical etching, etc. Further, the device contacts 42 and conductors 44 can include any suitable conductive material or conductive materials. In one or more embodiments, the electronic device 40 can be electrically connected to other electronic circuitry or devices disposed on or adjacent the substrate 30 or within the housing 20.

The electronic device 40 can be electrically connected to device contacts 42 using any suitable technique or techniques. For example, in one or more embodiments, solder bumps and/or contact pads of the electronic device 40 can be directly attached to one or more contacts 42 using any suitable technique or techniques, e.g., soldering, welding, laser bonding, mechanically connecting (e.g., direct-pressure contacts), etc. In one or more embodiments, one or more conductors 44 can be electrically connected to one or more device contacts 42 and one or more solder bumps and/or contact pads of the electronic device 40 using any suitable technique or combination of techniques, e.g., soldering, welding, laser bonding, mechanically connecting (e.g., direct-pressure contacts), etc.

Any suitable technique or techniques can be utilized to dispose the device contacts 42 and the conductors 44 on the substrate 30, e.g., the techniques described in U.S. patent application Ser. No. 14/976,475 to Sandlin et al. and entitled KINETICALLY LIMITED NANO-SCALE DIFFUSION BOND STRUCTURES AND METHODS. For example, electromagnetic radiation can be directed through substrate 30 from the second major surface 34 to a region between the device contacts 42, the conductors 44, and the substrate 30. The electromagnetic radiation can form a bond that seals the device contacts 42 and the conductors 44 to the substrate 30 in any suitable pattern or shape. The bond can be a laser bond.

The package 10 can also include power source 50. Any suitable power source or combination of power sources can be utilized with package 10, e.g., one or more batteries, capacitors, inductive-coupled energy devices, photovoltaic devices, beta-voltaic devices, alpha-voltaic devices, and thermo-electric devices.

The power source 50 can be disposed in any suitable location. In one or more embodiments, the power source 50 is disposed at least partially within the housing 20. As used herein, the term "at least partially within" means that at least a portion of the power source 50 is disposed within the housing 20. In one or more embodiments, the entire power source 50 can be disposed within the housing 20. In one or more embodiments, the power source 50 can include its own housing or casing. In one or more embodiments, the housing 20 provides at least a portion of an outer casing for the power source 50. For example, the inner surface 22 of the housing 20 can provide a portion of a casing of the power source 50, and a separate cover or protective layer can be disposed within the housing such that the power source is between the protective layer and the inner surface of the housing. The power source 50 can be integral with the housing 20. In one or more embodiments, the power source 50 is an element that is separately manufactured and then disposed within the housing 20.

The power source 50 includes one or more power source contacts 52, 54. Although depicted as including three contacts 52, 54 the power source 50 can include any suitable number of contacts that can be electrically connected to one or more devices to provide electrical energy to such devices from the power source. The power source contacts 52, 54 can be disposed in any suitable location relative to the power source 50. As illustrated in FIG. 2, the power source contacts 52, 54 are disposed at a first end 53 of the power source 50.

The power source contacts 52, 54 can include any suitable contact, e.g., the same contacts described regarding device contacts 42. In one or more embodiments, the power source contacts 52, 54 can include one or more compressible or resilient members that can engage one or more device contacts, e.g., device contacts 42, when the substrate 30 is sealed to the housing 20. Each power source contact 52 can be the same contact or type of contact. In one or more embodiments, each power source contact 52 can be different from each additional power source contact. For example, as illustrated in FIG. 2, the power source 50 includes an additional power source contact 54 that can be the same as or different from the power source contacts 52.

The electronic device 40 can, in one or more embodiments, be electrically connected to the power source 50 using any suitable technique or techniques. In one or more embodiments, the electronic device 40 can be electrically connected to the power source 50 when the substrate 30 is sealed to the housing 20. Any suitable technique or techniques can be utilized to electrically connect the electronic device 40 to the power source 50 when the substrate 30 is sealed to the housing 20. For example, one or more power source contacts 52, 54 can be electrically connected to one or more device contacts 42 when the substrate 30 is sealed to the housing 20. Any suitable electrical coupling between the power source contacts 52, 54 and the device contacts 42 can be utilized. In one or more embodiments, a non-bonded electrical connection can be formed between one or more device contacts 42 and one or more power source contacts 52, 54 when the substrate 30 is sealed to the housing 20. As used herein, the term "non-bonded electrical connection" means that an electrical connection is formed between two or more contacts, terminals, electrodes, etc., that can be maintained by suitable contact pressure between the two or more contacts to maintain the electrical connection, without the use of a bonding agent, e.g., a conductive adhesive, solder, etc. In one or more embodiments, this non-bonded electrical connection can be formed between one or more device contacts 42 and one or more power source contacts 52, 54 by mechanical engagement between such contacts using any suitable connecting element or elements, e.g., pin and sleeve connecting elements. In one or more embodiments, at least one of the device contacts 42 or the power source contacts 52, 54 can include a compressible or resilient member that mechanically engages another contact when the substrate 30 is sealed to the housing 20. In one or more embodiments, a bonded electrical connection can be provided between the one or more power source contacts 52, 54 and the one or more device contacts 42 using any suitable technique, e.g., welding, adhering using a conductive adhesive (e.g., UV or thermally curable adhesives), soldering, laser bonding, etc.

The substrate 30 can be sealed to the housing 20 using any suitable technique or techniques, e.g., mechanically fastening, adhering, press fitting, laser bonding, magnetic coupling, etc. In one or more embodiments, the substrate 30 is sealed to the housing 20 using a bonding ring 28. The bonding ring 28 includes a first major surface 27 that is bonded to the housing 20 and a second major surface 29 that is bonded to the substrate 30. The bonding ring 28 can include any suitable material or materials, e.g., copper, silver, titanium, niobium, zirconium, tantalum, stainless steel, platinum, iridium, or combinations thereof. In one or more embodiments, the bonding ring 28 can include a dielectric material or materials to provide a dielectric bonding ring, e.g., the same materials described herein regarding the substrate 30. Further, the bonding ring 28 can take any suitable shape and have any suitable dimensions. The bonding ring 28 can be disposed between the first major surface 32 of the substrate 30 and the housing 20. In one or more embodiments, the bonding ring 28 can be hermetically sealed to one or both of the first major surface 32 of the substrate 30 and the housing 20. The bonding ring 28 can be sealed to one or both of the substrate 30 and the housing 20 using any suitable technique or combination of techniques, e.g., laser bonding. In one or more embodiments, the bonding ring 28 is first attached to the first major surface 32 of the substrate 30 and then attached to the housing 20. In one or more embodiments, the bonding ring 28 is first attached to the housing 20 and then to the first major surface 32 of the substrate 30.

In one or more embodiments, the bonding ring 28 can be hermetically sealed to the housing 20 using any suitable technique or techniques, e.g., the techniques described in co-owned and co-filed U.S. patent application Ser. No. 14/976,475 to Sandlin et al. and entitled KINETICALLY LIMITED NANO-SCALE DIFFUSION BOND STRUCTURES AND METHODS. In one or more embodiments, electromagnetic radiation (e.g., light) can be directed through the bonding ring 28 from its second major surface 29 and focused at a region between the first major surface 27 of the bonding ring and the housing 20. Any suitable electromagnetic radiation can be utilized to form the bond. In one or more embodiments, the electromagnetic radiation can include laser light that can include any suitable wavelength or range of wavelengths. In one or more embodiments, the laser light can include light having a wavelength of at least 200 nm. In one or more embodiments, the laser light can include a wavelength of no greater than 2000 nm. For example, laser light can include UV light, visible light, IR light, and combinations thereof. The UV light can be provided by a UV laser that has any suitable wavelength or range of wavelengths and any suitable pulse width. In one or more embodiments, a UV laser can be utilized to provide light having a wavelength in a range of 100-400 nm and a pulse width in a range of 1-100 ns. In one or more embodiments, the materials for the substrate 30 and the housing 20, and the power level and wavelength of the light used may be selected such that the light may not directly damage, ablate, warp, or cut the substrate and the housing, and such that the substrate and the housing retain their bulk properties.

In general, light can be provided by any suitable laser or laser system. For example, the laser may generate light having a relatively narrow set of wavelengths (e.g., a single wavelength). In one or more embodiments, the light emitted by the laser may form a collimated beam that may not be focused at a particular point. In one or more embodiments, the light emitted by the laser may be focused at a focal point at a region between the first major surface 27 of the bonding ring 28 and the housing 20 to generate a laser bond.

Although the laser may provide light that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., TI sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, a power level of the laser may be set to approximately 1 W, distributed across the approximate focused beam diameter of 10 μm, with a top hat, Gaussian, or other suitable spatial energy profile.

The first major surface 32 of the substrate 30 can be bonded to the second major surface 29 of the bonding ring 28 using any suitable technique or techniques. In one or more embodiments, the first major surface 32 of the substrate 30 can be bonded to the second major surface 29 of the bonding ring 28 utilizing typical wafer-to-wafer bonding techniques, e.g., direct bonding, surface activated bonding, anodic bonding, eutectic bonding, glass frit bonding, adhesive bonding, thermocompression bonding, reactive bonding, and transient liquid phase diffusion bonding.

As mentioned herein, one or more electronic devices 40 can be disposed on the first major surface 32 of the substrate 30. In one or more embodiments, one or more additional devices or features can also be disposed on the second major surface 34 of the substrate 30. For example, in the embodiment illustrated in FIGS. 1-4, the first electrode 74 and the second electrode 76 are disposed on the second major surface 34 of the substrate 30. The first and second electrodes 74, 76 can include any suitable electrode or combination of electrodes and can take any suitable shape and have any suitable dimensions.

One or both of the first and second electrodes 74, 76 can be utilized to electrically connect the package 10 to any suitable device or devices that are external to the package. For example, one or both of the first and second electrodes 74, 76 can electrically connect the package 10 to a lead of an implantable medical device. In one or more embodiments, one or both of the first and second electrodes 74, 76 can electrically connect the package 10 to one or more additional power sources. Further, in one or more embodiments, one or both of the first and second electrodes 74, 76 can be therapeutic electrodes that can be utilized for delivering and/or receiving one or more electrical signals to or from a patient, either while the package is external or internal to a patient. Any suitable technique or combination of techniques can be utilized to electrically connect the package 10 to one or more devices through one or both of the first electrode 74 and second electrode 76, e.g., soldering, physical contact, welding, etc. The first and second electrodes 74, 76 can include any suitable conductive material or combination of conductive materials, e.g., copper, silver, titanium, niobium, zirconium, tantalum, stainless steel, platinum, iridium, or combinations thereof. In one or more embodiments, the first and second electrodes 74, 76 can include two or more materials, e.g., bi-metals, clad laminates, etc.

Further, the first and second electrodes 74, 76 can take any suitable shape or combination of shapes. In one or more embodiments, the first and second electrodes 74, 76 can take a circular shape in a plane parallel to the second major surface 34 of the substrate 30. In one or more embodiments, the first and second electrodes 74, 76 can take a rectangular shape in the plane parallel to the second major surface 34. Further, the first and second electrodes 74, 76 can take any suitable shape or combination of shapes in a plane orthogonal to the second major surface 34, e.g., square, tapered, domed, etc. In one or more embodiments, the first and second electrodes 74, 76 can include complex shapes such as grooves or channels formed in the electrode to facilitate attachment of conductors or electronic devices to the contacts.

The first and second electrodes 74, 76 can also include any suitable dimensions. In one or more embodiments, the first and second electrodes 74, 76 can have any suitable thickness in a direction normal to the second major surface 34 of the substrate 30. In one or more embodiments, this thickness can be at least 10 micrometers. In one or more embodiments, the thickness can be no greater 200 micrometers. In one or more embodiments, the first and second electrodes 74, 76 can be of sufficient size and thickness to enable laser, resistance, or other welding and joining techniques to be utilized to electrically couple conductors and/or electronic devices to the electrode.

The first and second electrodes 74, 76 can be electrically connected to one or more electronic devices disposed on or within the package, e.g., electronic device 40. Any suitable technique or combination of techniques can be utilized to electrically connect one or both of the first and second electrodes 74, 76 to one or more devices disposed on or within the housing. In one or more embodiments, the first electrode 74 can be electrically connected to device 40 through via 78 (FIG. 3), which is electrically connected to device 40 through conductor 75. Via 78 can be formed between the first major surface 32 and the second major surface 34 of the substrate 30, and a conductive material can be disposed within the via using any suitable technique or techniques. Similarly, second electrode 76 can be electrically connected to electronic device 40 through via 79 (FIG. 3), which is electrically connected to the device through conductor 77. Once again, via 79 can be formed between the first major surface 32 and the second major surface 34 of substrate 30, and conductive material can be disposed within the via using any suitable technique or combination of techniques.

The package 10 of FIGS. 1-4 can also include a conductor 70 disposed on the second major surface 34 of the substrate 30 or within the substrate between the first major surface 32 and the second major surface 34. The conductor 70 can include any suitable shape or combination of shapes and can be formed using any suitable conductive material. Although depicted as including one conductor 70, two or more conductors can be formed on the second major surface 34 of the substrate 30 or within the substrate. Further, the conductor 70 can be patterned to include any suitable shape or combination of shapes.

In one or more embodiments, the conductor 70 can be formed to provide an antenna, and the package 10 can be wirelessly coupled to a device or system through such antenna. Further, in one or more embodiments, the conductor 70 can form an inductive coil that can be utilized to provide inductive coupling to one or more external devices, e.g., one or more inductive power sources.

The conductor 70 can be electrically connected to one or more electronic devices disposed within the housing of the package 10 using any suitable technique or combination of techniques. For example, a via 72 (FIG. 3) can be formed between the first major surface 32 and the second major surface 34 of the substrate 30 that is that is electrically connected to, e.g., electronic device 40 through conductor 73. Conductive material can be disposed within via 72 that electrically connects the conductor 72 electronic device 40. The conductor 70 can be electrically connected to the via 72 using any suitable technique or combination of techniques.

Figure 5:
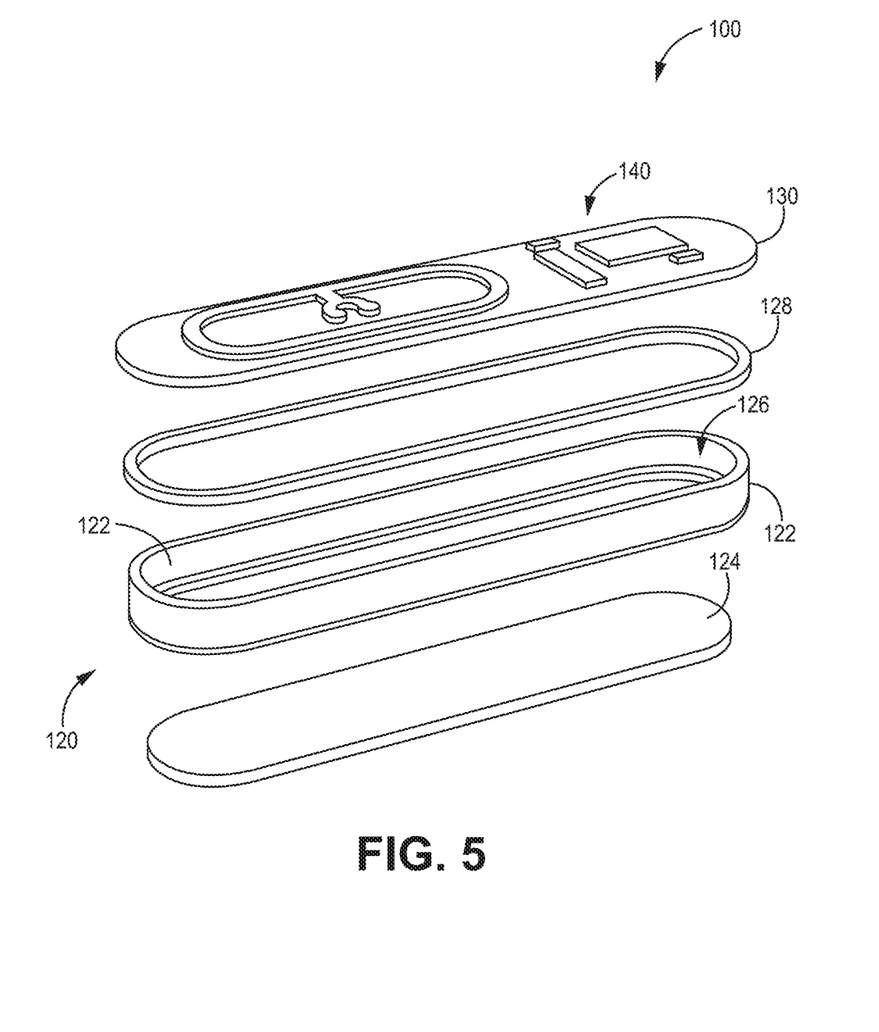
FIG. 5 is a schematic exploded top perspective view of another embodiment of a sealed package.

The various embodiments of sealed packages described herein can include a unitary housing or one that includes two or more separately-manufactured parts that are subsequently connected together using any suitable technique or techniques. For example, FIG. 5 is a schematic exploded view of another embodiment of a sealed package 100. All of the design considerations and possibilities regarding the sealed package 10 of FIGS. 1-4 apply equally to the sealed package 100 of FIG. 5.

One difference between the package 100 of FIG. 5 and package 10 of FIGS. 1-4 is that housing 120 includes a sidewall 122 and a bottom wall 124 that is connected to the sidewall. The sidewall 122 and the bottom wall 124 form a cavity 126 of the housing 120 having an inner surface 122. The bottom wall 124 can be connected to the sidewall 122 using any suitable technique or techniques, e.g., conventional metal laser welding, epoxies, etc.

The bottom wall 124 can include any suitable material or materials. In one or more embodiments, the bottom wall 124 includes a material that is different from material utilized to form the sidewall 122. In one or more embodiments, the bottom wall 124 and the sidewall 122 include the same material or materials.

As is described further herein, the housing 120 that includes the sidewall 122 and a separate bottom wall 124 can enable assembly of the sealed package 100 such that all wafer preparation and bonding is completed without having a power source disposed at least partially within the housing during such processing. In one or more embodiments, the bonding ring 128 can be connected to the sidewall 122 of the housing using any suitable technique or techniques, e.g., high-temperature diffusion bonding. The substrate 130 can then be connected to the bonding ring 128 using any suitable technique or techniques, e.g., low-temperature diffusion bonding, such that the substrate is sealed to the sidewall. A power source can then be disposed at least partially within the housing 120 and electrically connected to one or more electronic devices 140 disposed on the substrate 130 after the substrate is connected to the sidewall of the housing via bonding ring 128. In one or more embodiments, the bottom wall 124 can then be connected to the sidewall 122 of the housing 120 using any suitable technique or techniques, e.g., laser welding, to form sealed package 100.

Figure 6:
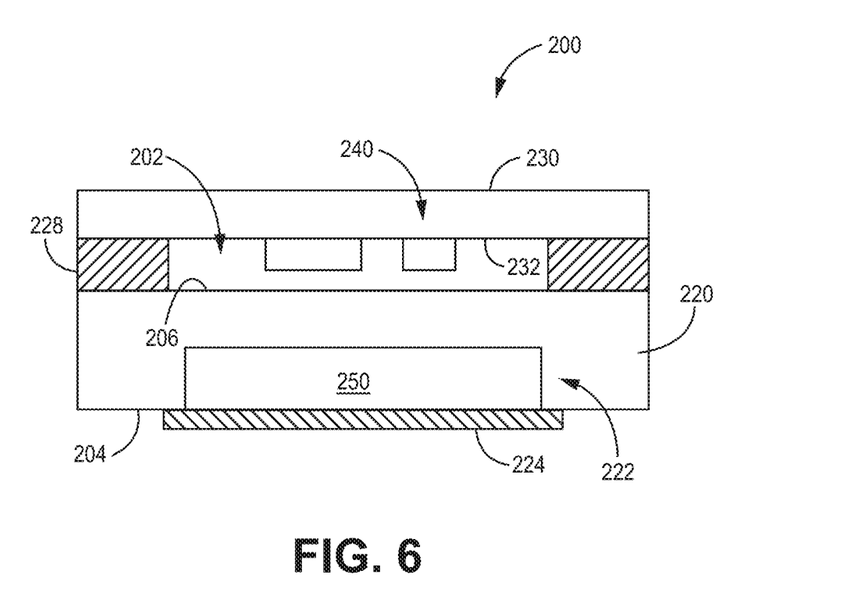
FIG. 6 is a schematic cross-section view of another embodiment of a sealed package.

FIG. 6 is a schematic cross-section view of another embodiment of a sealed package 200. All of the design considerations and possibilities regarding the package 10 of FIGS. 1-4 and the package 100 of FIG. 5 apply equally to the package 200 of FIG. 6. The package 200 includes a housing 220 having a first major surface 204, a second major surface 206, and a cavity 222 disposed in the first major surface. The housing 220 also includes a bottom wall 224 that is disposed on the first major surface 204 of the housing to enclose the cavity 222. The package also includes a dielectric substrate 230 having a major surface 232, and a dielectric bonding ring 228 disposed between the first major surface of the dielectric substrate and the second major surface 206 of the housing. The dielectric bonding ring 228 is hermetically sealed to both the major surface 232 of the dielectric substrate 230 and the second major surface 206 of the housing 220. The dielectric substrate 230, the dielectric bonding ring 228, and the second major surface 206 of the housing 220 form a second cavity 202. The package also includes an electronic device 240 disposed on the major surface 232 of the dielectric substrate 230 and within the second cavity 202. Further, the package includes a power source 250 disposed at least partially within the cavity 222 of the housing 220 and electrically connected to the electronic device 240.

One difference between package 200 of FIG. 6 and package 10 of FIGS. 1-4 is that package 200 includes the second cavity 202 formed by the dielectric substrate 230, the bonding ring 228, and the second major surface 206 of the housing 220. One or more electronic devices 240 disposed on the major surface 232 of the substrate 230 can be disposed within the second cavity 202 when the major surface of the substrate is connected to the bonding ring 228 using any suitable technique or techniques. Unlike the package 10 of FIGS. 1-4, power source 250 and electronic device 240 are not disposed within the same cavity of the housing. Instead, the power source 250 is disposed within the cavity 222 that is disposed in the first major surface 204 of the housing 204 and sealed by the bottom wall 224 of the housing, while electronic device 240 is disposed within second cavity 202. And suitable technique or techniques can be utilized to electrically connect the power source 250 to the electronic device 240. In one or more embodiments, one or more vias can be disposed through the housing 220 between the cavity 222 and the second cavity 202 to electrically connect the power source 250 to the electronic device 240.

Package 200 can be assembled using any suitable technique or techniques. For example, in one or more embodiments, cavity 222 can be formed in the first major surface 204 of the housing 220 using any suitable technique or techniques. The bonding ring 228 can be disposed on the second major surface 206 of the housing 220 using any suitable technique or techniques, e.g., diffusion bonding. Power source 250 can be disposed within cavity 222, and the bottom wall 224 can be connected to the first major surface 204 of the housing 220 using any suitable technique or techniques. Substrate 230 can be connected to the housing 220 via bonding ring 228 using any suitable technique or techniques (e.g., laser bonding) such that one or more electronic devices 240 disposed on the major surface 232 of the substrate can be disposed within the second cavity 202.

As mentioned herein, the various embodiments of sealed packages can be manufactured using any suitable technique or techniques. For example, FIGS. 7A-D are various schematic views of one embodiment of a method 300 for manufacturing sealed package 10 of FIGS. 1-4. Although described in reference to sealed package 10, the method 300 can be utilized to manufacture any suitable sealed package, e.g., sealed package 100 of FIG. 5 and sealed package 200 of FIG. 6. The method 300 is described as a wafer-to-wafer manufacturing process. In one or more embodiments, the various embodiments of sealed packages described herein can be manufactured as individual packages using any suitable technique or techniques.

Figure 7A:
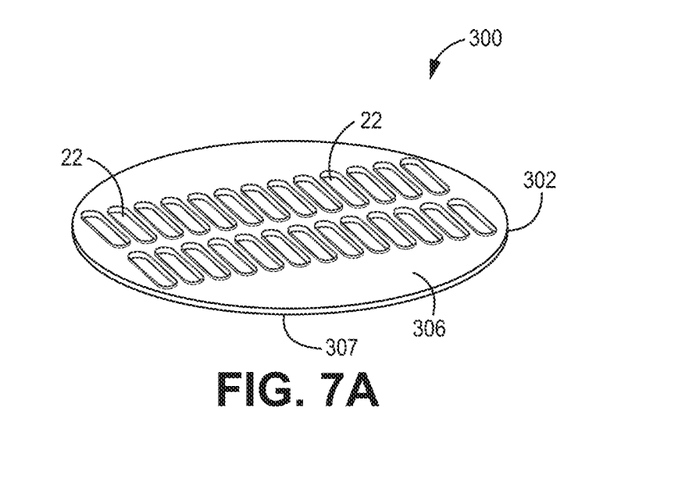
FIG. 7A is a schematic perspective view of disposing one or more cavities in a housing wafer.
Figure 7B:
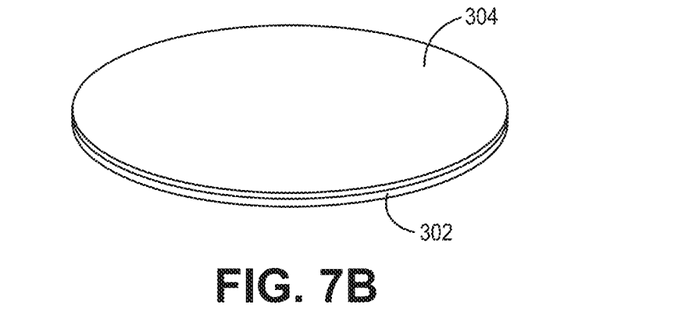
FIG. 7B is a schematic perspective view of sealing a bonding wafer to a first major surface of the housing wafer.

As shown in FIG. 7A, one or more cavities 22 can be disposed in a housing wafer 302 using any suitable technique or techniques, e.g., etching, ablation, laser cutting, water jet cutting, mechanical material removal, etc. The housing wafer 302 can include any suitable material or materials, e.g., the same materials described herein regarding housing 20 of sealed package 10 of FIGS. 1-4. A bonding wafer 304 can be sealed to a first major surface 306 of the housing wafer 302 using any suitable technique or techniques as shown in FIG. 7B. The bonding wafer 304 can include any suitable material or materials, e.g., the same materials described herein regarding bonding ring 28 of sealed package 10 of FIGS. 1-4. In one or more embodiments, the bonding wafer 304 can be diffusion bonded to the first major surface 306 of the housing wafer 302 such that the bonding wafer is hermetically sealed to the housing wafer. In one or more embodiments, the bonding wafer 304 can be high-temperature diffusion bonded to the housing wafer 302.

Figure 7C:
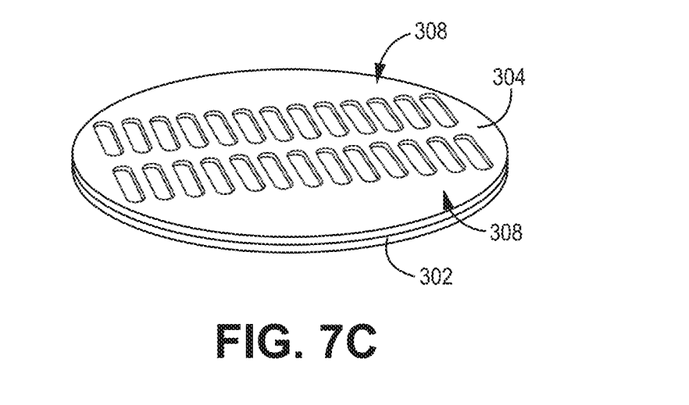
FIG. 7C is a schematic perspective view of disposing one or more openings in the bonding wafer to expose the one or more cavities of the housing wafer.

As shown in FIG. 7C, one or more openings 308 can be disposed in the bonding wafer 304 to expose one or more of the cavities 22 of the housing wafer 302. Any suitable technique or techniques can be utilized to dispose the one or more openings 308 in the bonding wafer 304, e.g., at least one of etching, laser excising, fracture cutting, or cutting the opening into the bonding wafer to expose the one or more cavities 22 of the housing wafer 302. The openings 308 can each take any suitable shape and have any suitable dimensions. In one or more embodiments, one or more openings 308 can take the same shape and have the same dimensions as the cavity 22 with which it is associated. In one or more embodiments, the bonding wafer 304 can be resurfaced after the opening or more openings 308 have been disposed therein using any suitable technique or techniques that are generally employed in wafer surface preparation, e.g., abrasive media polishing.

Figure 7D:
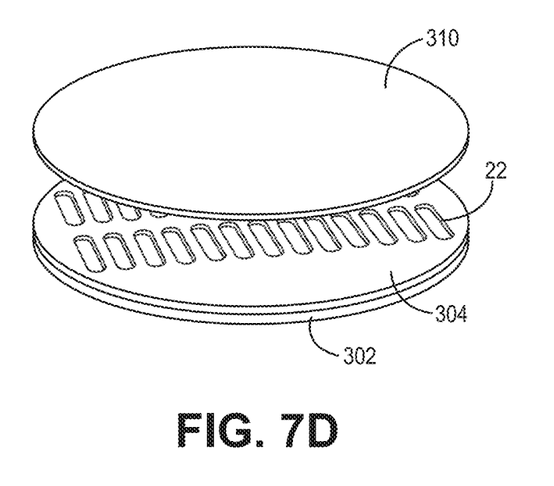
FIG. 7D is a schematic perspective view of sealing a substrate wafer to the bonding wafer.

A substrate wafer 310 can be provided in FIG. 7D that can, in one or more embodiments, include on or more electronic devices (e.g., electronic device 40 of FIGS. 1-4) disposed on one or both major surfaces of the substrate wafer (not shown). In one or more embodiments, one or more electronic devices can be formed on the substrate wafer 310 using any suitable technique or techniques. The substrate wafer 310 can be sealed to the bonding wafer 304 using any suitable technique or techniques such that one or more of the electronic devices are in registration with a cavity 22 of the housing wafer 302. As used herein, the term "in registration with" means that at least a portion of one or more electronic devices disposed on the substrate wafer 310 are disposed within an opening 308 of the bonding wafer 304 that exposes a cavity 22 of the housing wafer 302. In one or more embodiments, the substrate wafer 310 can be diffusion bonded to the bonding wafer 304 such that the substrate wafer is hermetically sealed to the bonding wafer. In one or more embodiments, the substrate wafer 310 can be low-temperature diffusion bonded to the bonding wafer 304. Further, in one or more embodiments, the substrate wafer 310 can be laser bonded to the bonding wafer 304.

Although not shown, one or more power sources (e.g., power source 50 of FIGS. 1-4) can be disposed at least partially within one or more cavities 22 of the housing wafer 302 prior to sealing the substrate wafer 310 to the dielectric bonding wafer 304. The power source can be electrically connected to one or more electronic devices disposed on the substrate wafer 310 utilizing any suitable technique or techniques. Further, in embodiments wherein the housing 20 includes a sidewall and a separate bottom wall (e.g., package 100 of FIG. 5), the cavity 22 formed in the housing wafer 302 can be an opening that extends between the first major surface 306 and a second major surface 307 of the housing wafer. A power source can be disposed in one or more cavities or openings 22 of the housing wafer 302 after the substrate wafer 310 is sealed to the bonding wafer 308. A bottom wall (e.g., bottom wall 124 of housing 120 of FIG. 5) can be sealed to the second major surface 307 of the housing wafer 302 over the opening using any suitable technique or techniques such that the power source is disposed between the substrate wafer 310 and the bottom wall One or more portions of each of the housing wafer 302, dielectric bonding wafer 304, and substrate wafer 310 can be removed to form the hermetically-sealed package 10 utilizing any suitable technique or techniques, e.g., singulation.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A method of forming a hermetically-sealed package, comprising:
    disposing a cavity in a housing wafer;
    hermetically sealing a dielectric bonding wafer to a first major surface of the housing wafer;
    disposing an opening in the dielectric bonding wafer to expose the cavity of the housing wafer;
    disposing an electronic device on a substrate wafer;
    hermetically sealing the substrate wafer to the dielectric bonding wafer such that the electronic device is in registration with the cavity of the housing wafer, wherein the substrate wafer is hermetically sealed to the dielectric bonding wafer after the dielectric bonding wafer has been hermetically sealed to the first major surface of the housing wafer; and
    removing a portion of each of the housing wafer, dielectric bonding wafer, and substrate wafer to form the hermetically-sealed package.

2. The method of claim 1, further comprising disposing a power source in the cavity of the housing wafer prior to hermetically sealing the substrate wafer to the dielectric bonding wafer, wherein the power source is electrically connected to the electronic device.

3. The method of claim 1, wherein the cavity of the housing wafer comprises an opening that extends between the first major surface and a second major surface of the housing wafer, wherein the method further comprises:
    disposing a power source in the opening of the housing wafer after hermetically sealing the substrate wafer to the dielectric bonding wafer; and
    hermetically sealing a bottom wall to the second major surface of the housing wafer over the opening such that the power source is disposed between the substrate wafer and the bottom wall.

4. The method of claim 1, wherein the electronic device is disposed on a major surface of the substrate wafer, wherein hermetically sealing the substrate wafer to the dielectric bonding wafer comprises hermetically sealing the major surface of the substrate wafer to the dielectric bonding wafer such that the electronic device is disposed within the cavity of the housing wafer.

5. The method of claim 1, wherein hermetically sealing the dielectric bonding wafer comprises diffusion bonding the dielectric bonding wafer to the housing wafer.

6. The method of claim 5, wherein diffusion bonding the dielectric bonding wafer comprises laser bonding the dielectric bonding wafer to the housing wafer.

7. The method of claim 1, wherein hermetically sealing the substrate wafer to the dielectric bonding wafer comprises laser bonding the substrate wafer to the dielectric bonding wafer.

8. The method of claim 1, wherein disposing the electronic device on the substrate wafer comprises forming the electronic device on the substrate wafer.

9. The method of claim 1, wherein disposing the opening in the dielectric bonding wafer comprises at least one of etching, ablating, or mechanically removing material to dispose the opening in the dielectric bonding wafer to expose the cavity of the housing wafer.

10. The method of claim 1, wherein the dielectric bonding wafer comprises sapphire.

11. The method of claim 1, wherein the substrate wafer comprises a dielectric material.

12. The method of claim 11, wherein the substrate wafer comprises at least one of sapphire or glass.

13. The method of claim 1, wherein the housing wafer comprises a conductive material.

14. The method of claim 13, wherein the housing wafer comprises titanium.

* * * * *